(12) United States Patent
Hsia (10) Patent No.: US 6,383,155 B1
(45) Date of Patent: May 7, 2002

(54) PORTABLE WATER PICKS

(76) Inventor: Chih-Yu Hsia, 301 Warren Way, Arcadia, CA (US) 91007

( * ) Notice: Subject to any disclaimer, the term of this patent is extended or adjusted under 35 U.S.C. 154(b) by 24 days.

(21) Appl. No.: 09/766,928

(22) Filed: Jan. 23, 2001

(51) Int. Cl.[7] ............................................. A61H 7/00
(52) U.S. Cl. ................................................... 601/165
(58) Field of Search ................... 601/165, 162, 601/163, 164; 433/80

(56) References Cited

U.S. PATENT DOCUMENTS

| | | | | |
|---|---|---|---|---|
| 696,230 A | * | 3/1902 | Fielding | 285/8 |
| 1,798,884 A | * | 3/1931 | Hyatt | 285/8 |
| 3,208,145 A | * | 9/1965 | Turner | 433/95 |
| 3,581,998 A | * | 6/1971 | Roche | 239/415 |
| 3,753,435 A | * | 8/1973 | Basnick | 601/163 |
| 4,135,501 A | * | 1/1979 | Leunissan | 433/80 |
| 4,397,640 A | * | 8/1983 | Haug et al. | 604/33 |
| 4,928,675 A | * | 5/1990 | Thornton | 601/165 |
| 5,231,978 A | * | 8/1993 | Kao et al. | 601/165 |
| 5,385,533 A | * | 1/1995 | Coivello | 601/165 |
| 5,387,182 A | * | 2/1995 | Otani | 601/165 |

* cited by examiner

Primary Examiner—John J. Wilson (57) ABSTRACT

In apparatus to facilitate cleaning teeth with tap water the first combination comprising a gasket, a bucket, a tubing, a clamp, a handle, and a discharging tube; the second combination comprising a gasket, a bucket, a clamp, a container, two pieces of tubing, a handle, and a discharging tube; the third combination comprising a bucket, a tubing, a handle, and a discharging tube; the fourth combination comprising a bucket, a container, two pieces of tubing, a handle, and a discharging tube.

18 Claims, 12 Drawing Sheets

PORTABLE WATER PICKS

BACKGROUND OF THE INVENTION

1. Field of the Invention

This invention relates to water picks and particularly to portable water picks which allow a user to easily connect to a sink faucet to use the tap water to clean teeth or alike. This invention also introduces means that allow medicine or cleaning solutions to be mixed into the water jet for picking and cleaning actions.

2. Descriptions of the Prior Arts

No prior art related to portable water picks was found.

SUMMARY OF THE INVENTION

To clean food residuals between teeth sometime is difficult. Ordinary water picks which use small pumps to shoot water to clean between teeth are bulky, not suitable to carry around for travels, and noisy in use. Therefore, a small, easy to carry around, lightweight and quiet water pick is sought.

The invented devices provide means to connect a flexible tube to a spout of an existing sink faucet. The invented devices also provide means to create a small stream of high-speed water jet to be used to clean between teeth or the alike. The invented devices also provide means to easily handle and control the water jet. Means to mix medicine or cleaning solutions into the water jet are also included in the invented devices.

These and other objects and advantages of the invention, as well as the details of illustrative embodiments, will be more fully understood from the following specification and drawings, in which:

GENERAL DESCRIPTION

Five variations of the invented device are introduced herein in this specification.

Figure 1:
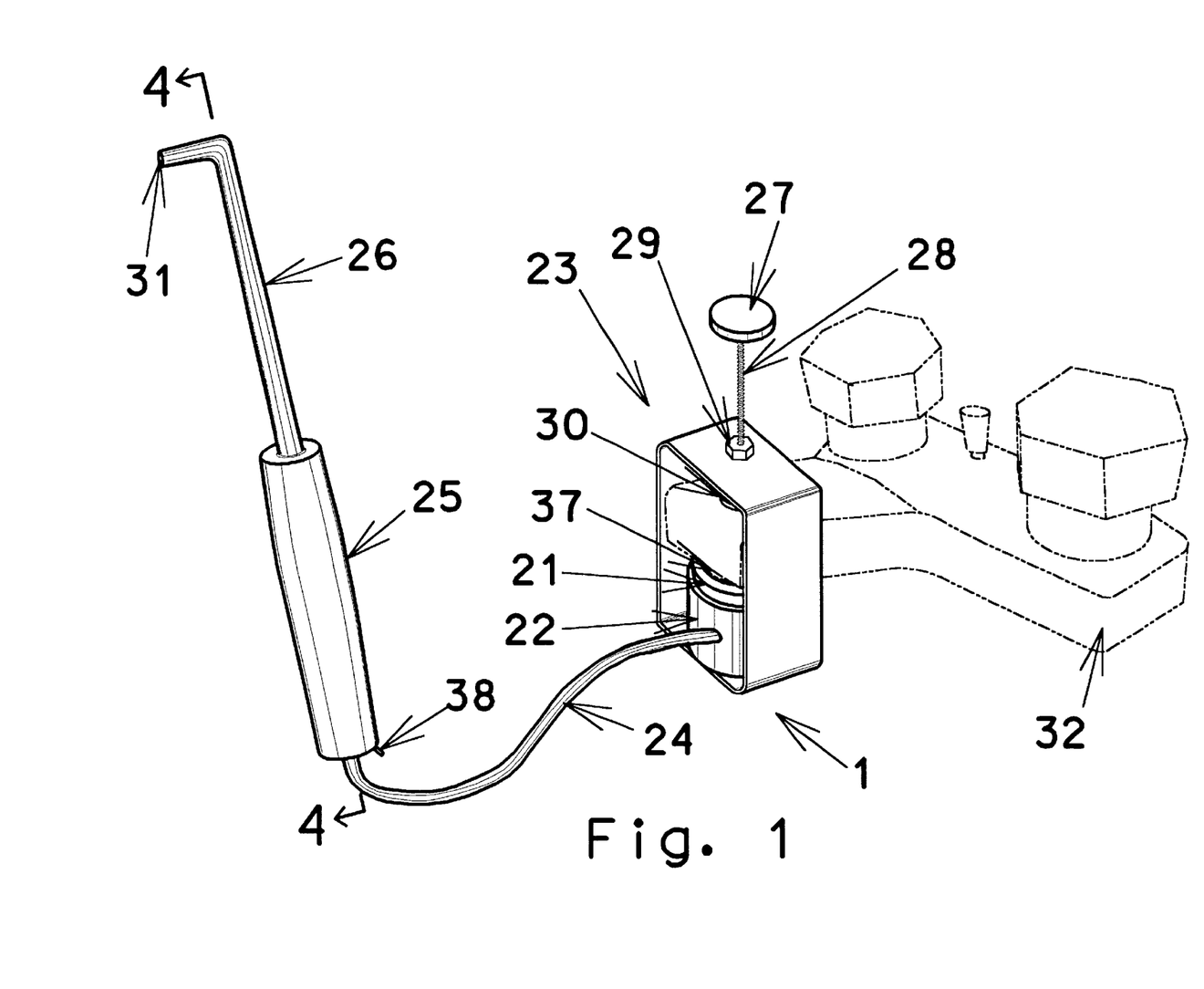
FIG. 1 is an isometric view of the first variation of the invented devices.

Referring to FIG. 1, the first variation of the invented portable water pick 1 consists of a cylindrical gasket 21, a bucket 22, a clamp 23, a tube 24, a handle 25, and a discharging header 26. The clamp 23 that is a "D"-shaped clamp that has a nut 29 on it top. An adjusting bolt 28 penetrates the nut. The adjustable bolt is a bolt with a swivel head or ball joint head 30 on one end and with an adjusting head or handle 27 on the other end.

Figure 2:
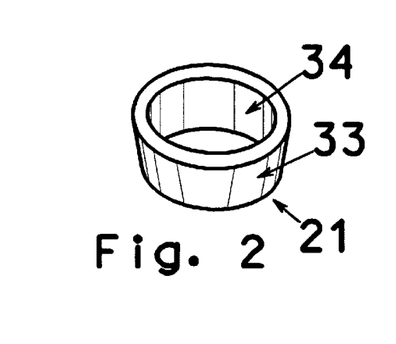
FIG. 2 is an isometric view of the gasket which is a component of the invented devices.
Figure 3:
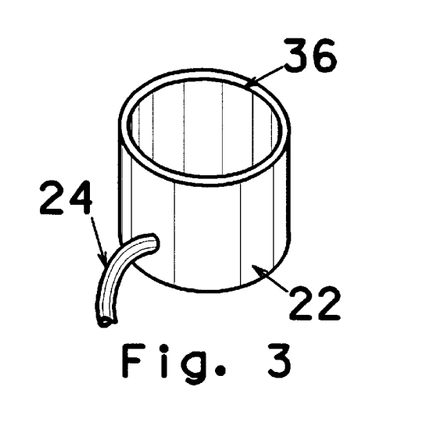
FIG. 3 is an isometric view of the bucket which has a portion of a tube connected.

Referring to FIGS. 1 and 2, the cylindrical gasket 21 is a gasket with tapered exterior side surface 33. The interior side surface 34 can snugly fit with the exterior side surface of an aerator 37 of a sink faucet 32. Referring to FIGS. 1 and 3, the bucket 22 is a small bucket that has a hole on its side wall. The tube 24 is a flexible tube and is mounted onto the bucket through the hole with the aids of a nipple or similar means.

Figure 4:
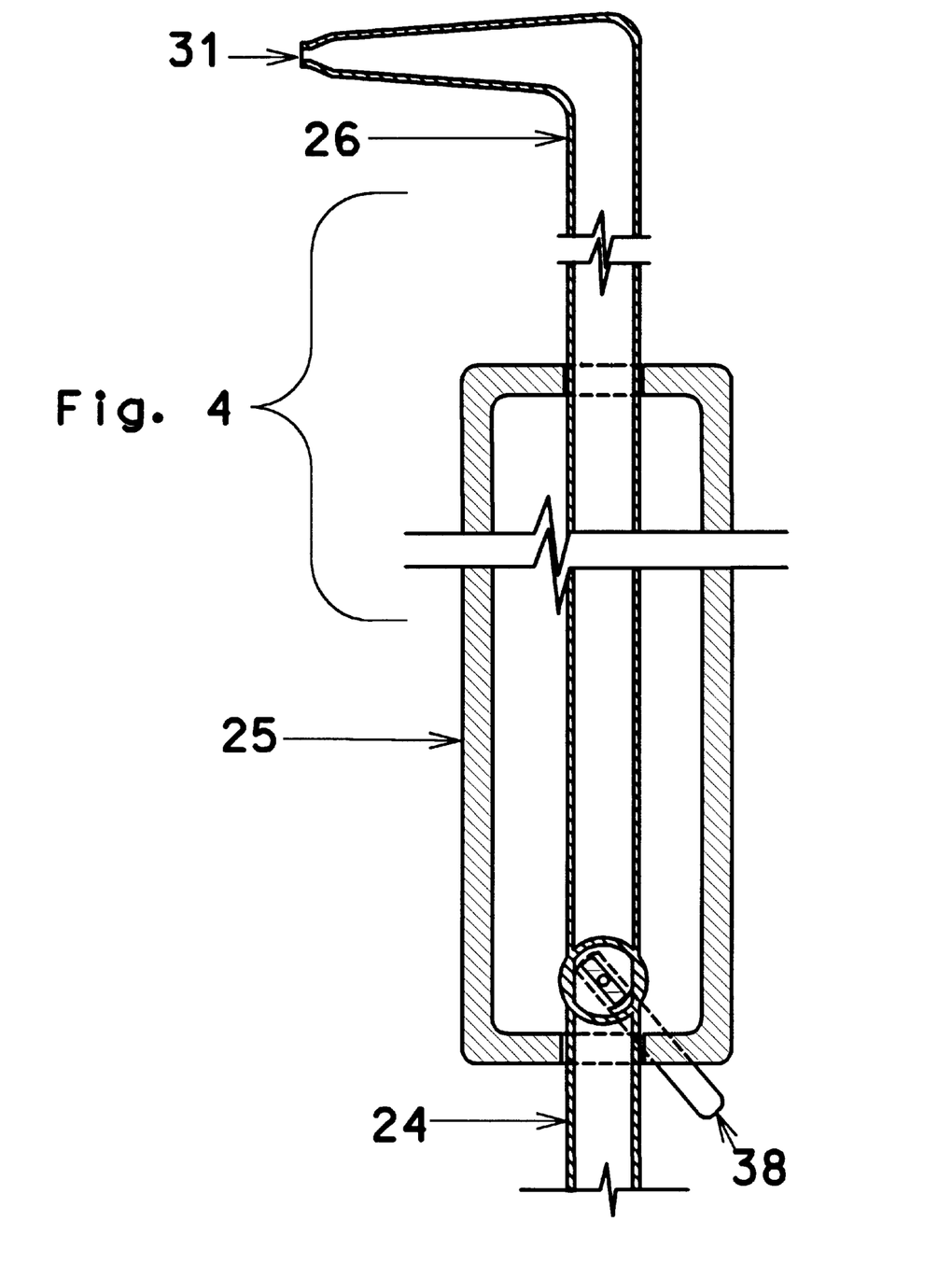
FIG. 4 is a sectional view of components shown in FIG. 1.

Referring to FIGS. 1 and 4, one end of the handle 25 connects with the tube 24. The other end of the handle connects with the discharging header 26. The discharging header is a relatively rigid tube with a sharp bend near its free end that reduces its correctional area and becomes a nozzle 31. The handle facilities the handling and controlling of the discharging header which in turn controls directions of fluid discharged from the nozzle. The handle also provides conduit to convey liquid from the tube to the discharging header. The handle has an optional flow control valve assembly 38 that can regulate the amount flow discharging through the nozzle.

Figure 5:
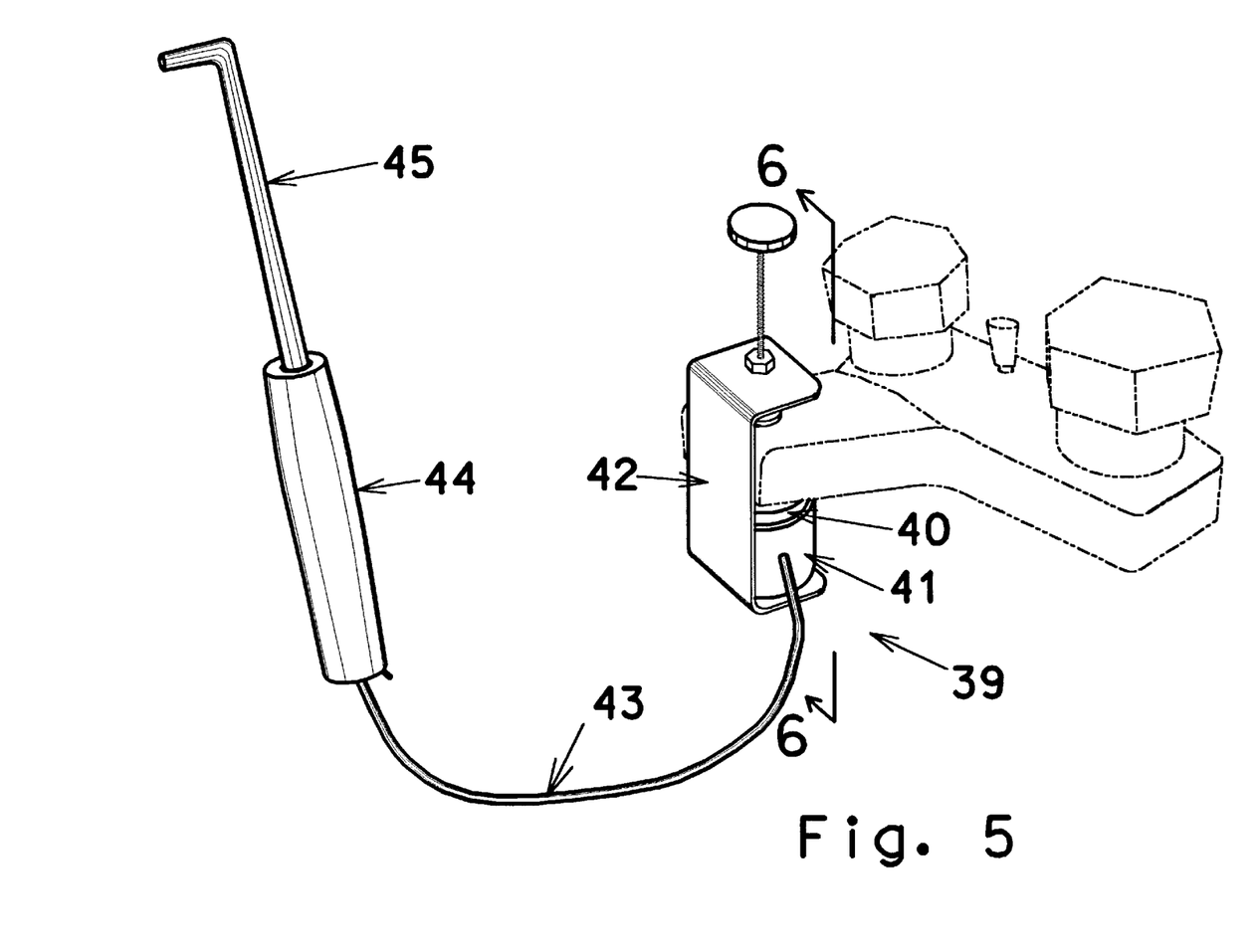
FIG. 5 is an isometric view of the second variation of the invented devices.
Figure 6:
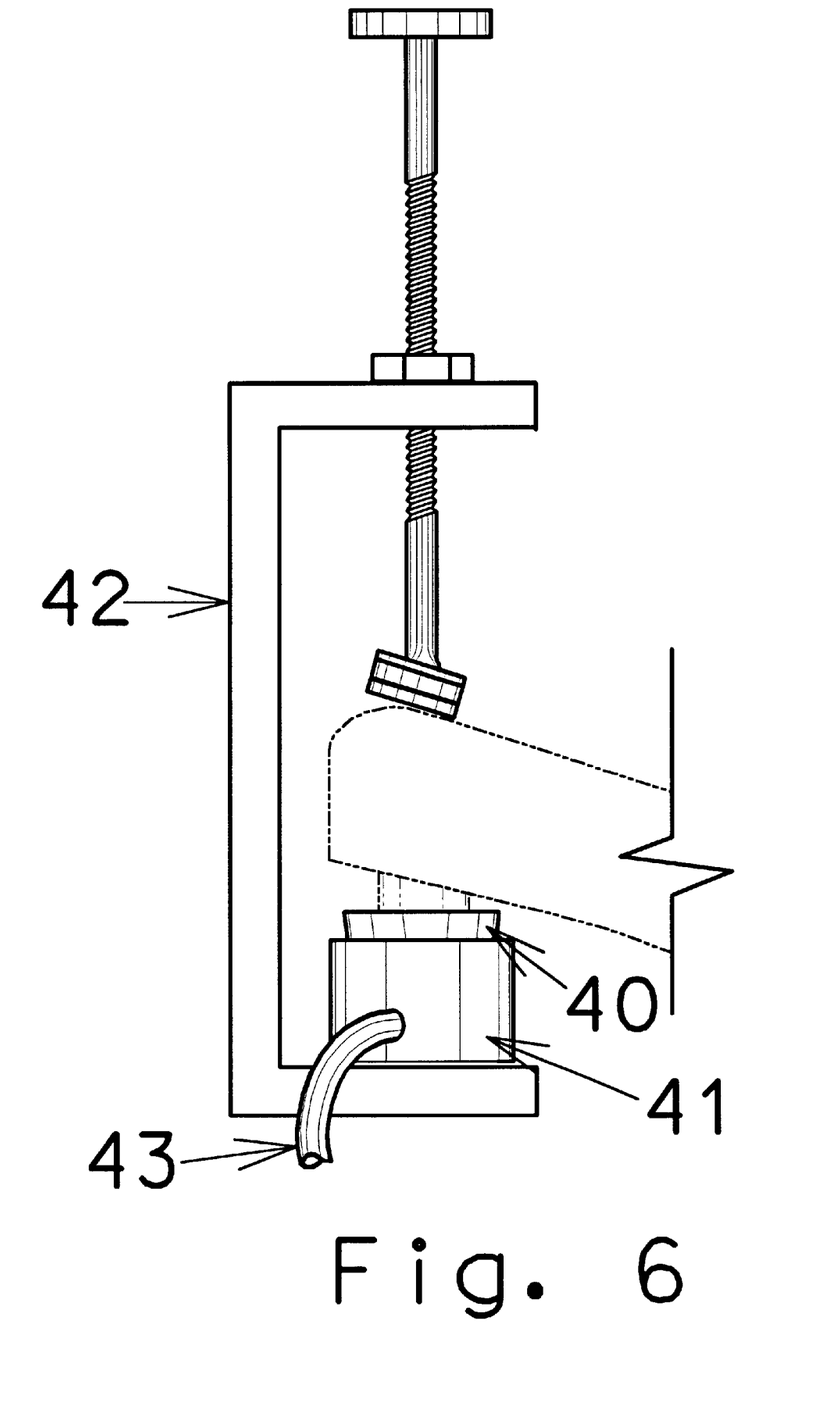
FIG. 6 is a side view of components shown in FIG. 5.

Referring to FIGS. 5 and 6, the second variation of the invented portable water pick 39 consists of a cylindrical gasket 40, a bucket 41, a clamp 42, a tube 43, a handle 44, and a discharging header 45. The gasket, the bucket, the tube, the handle and the discharging header are the same as those for the first variation of the invented devices. In lieu of a "D"-shaped clamp for the first invented devices the clamp 42 for this second variation is a "C"-shaped clamp which also has a nut and an adjusting bolt, just like those for the first variation's.

Figure 7:
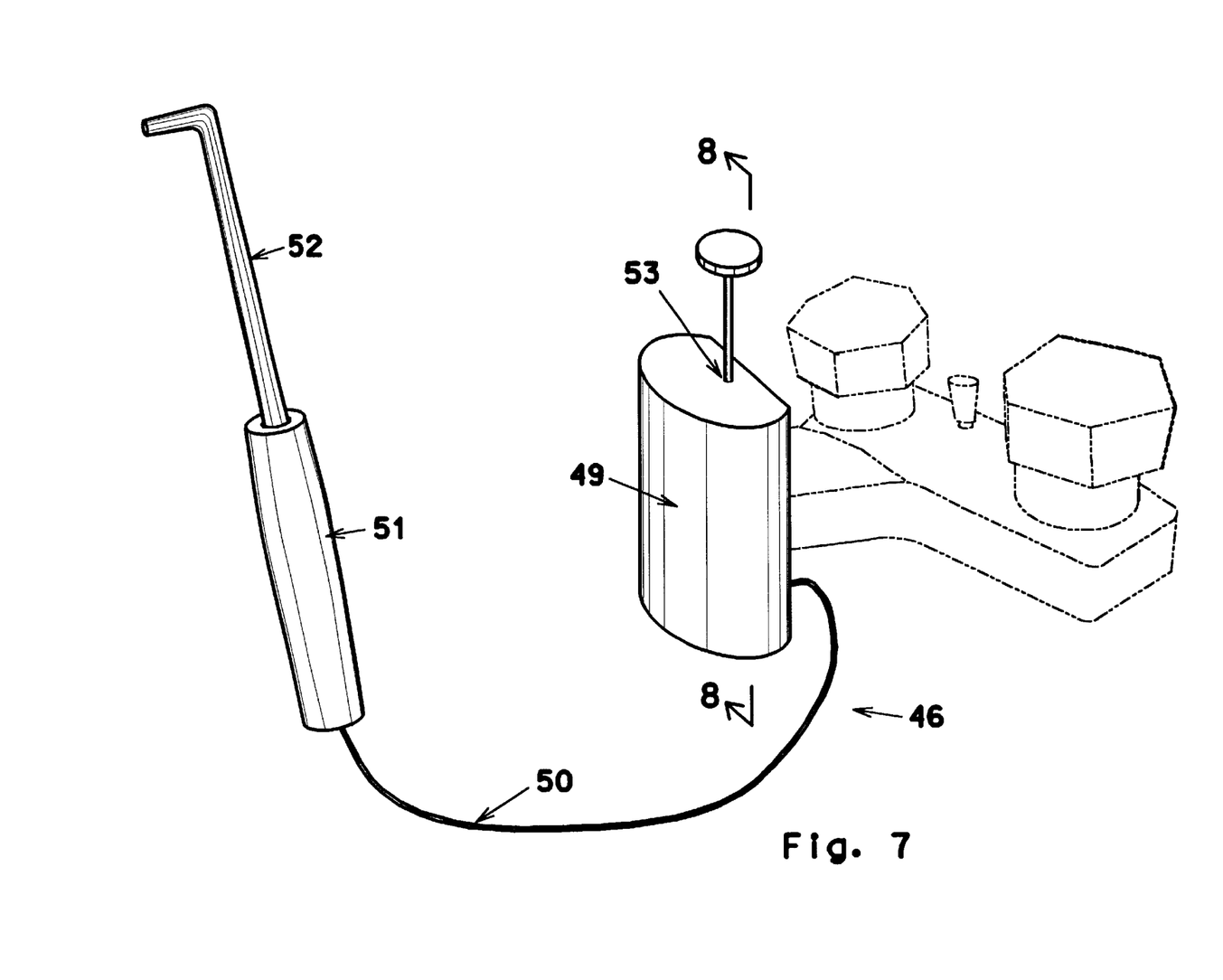
FIG. 7 is an isometric view of the third variation of the invented devices.
Figure 8:
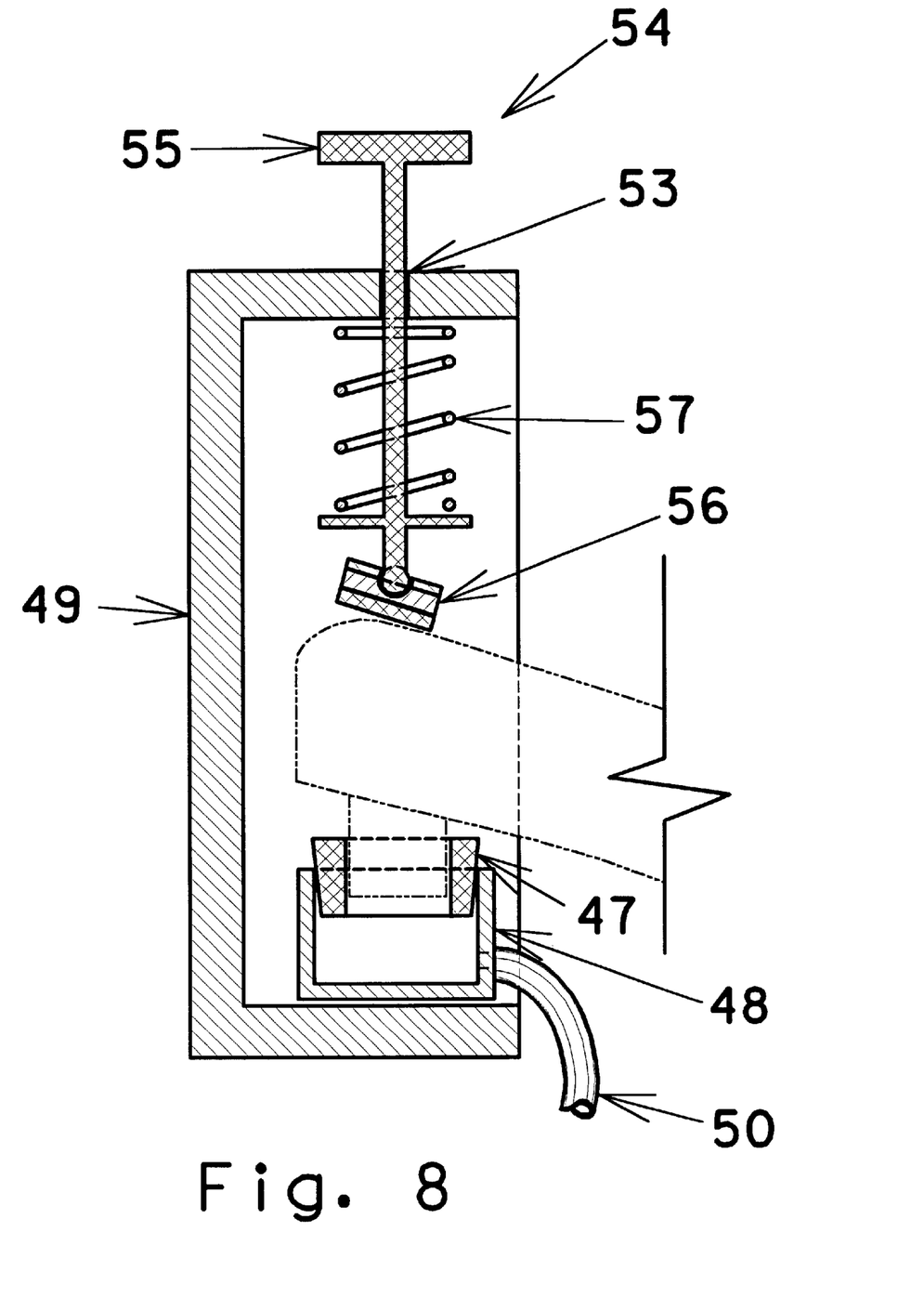
FIG. 8 is a sectional view of the components shown in FIG. 7.

Referring to FIGS. 7 and 8, the third variation of the invented portable water pick 46 consists of a cylindrical gasket 47, a bucket 48, a clamp 49, a tube 50, a handle 51, and a discharging header 52. The gasket, the bucket, the tube, the handle and the discharging header are the same as those for the first variation of the invented devices. In lieu of a "D"-shaped clamp for the first invented device the clamp 49 for this third variation resembles a side-opened bucket. A hole 53 is on the top of the "bucket". A spring-loaded adjuster 54 penetrates the hole. The spring-loaded adjuster is a rod with a plate or handle 55 on one end and with a swivel head or ball joint head 56 on the other end. A spring 57 that can push the swivel head or ball joint head away from the top of the clamp is mounted on the spring-loaded adjuster.

Although not illustrated herein the spring-loaded adjuster can alternatively be on the bottom of the clamp. The swivel head of the spring-loaded adjuster can push the bottom of the bucket upward toward the cylindrical gasket.

Figure 9:
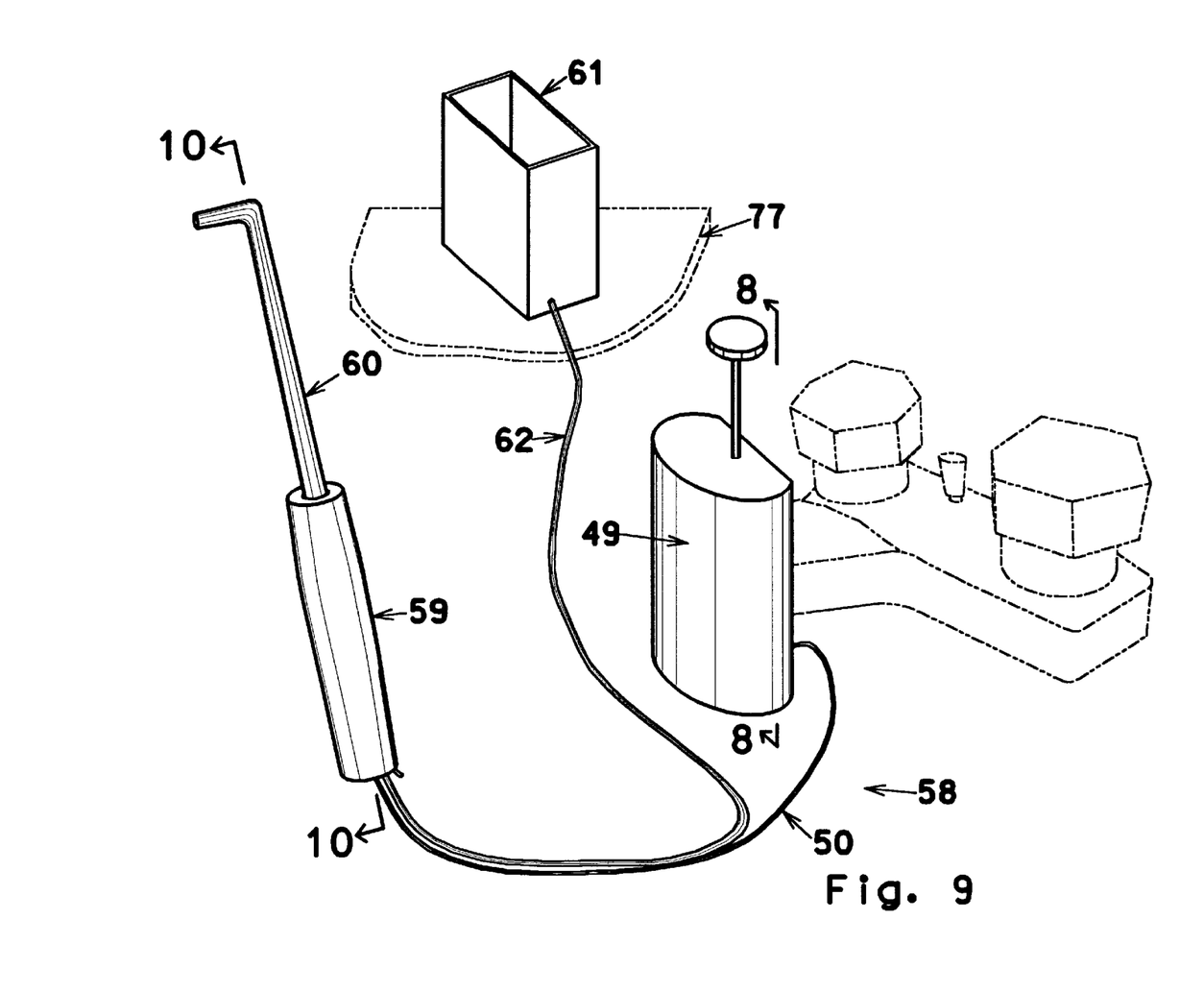
FIG. 9 is an isometric view of the fourth variation of the invented devices.

Referring to FIGS. 8 and 9, the fourth variation of the invented portable water pick 58 consists of a cylindrical gasket 47, a bucket 48, a clamp 49, a tube 50, a handle 59, a discharging header 60, a container 61, and a tube 62. The gasket, the bucket, the clamp, and the tube 50 are the same as those for the third variation of the invented devices. The container is a small bucket which can hold medicine or cleaning solutions. The container has a hole near its bottom. The tube 62 is a flexible tube. One end of the tube 62 connects with the hole of the container. The other end of the tube 62 connects with the handle 59.

Figure 10:
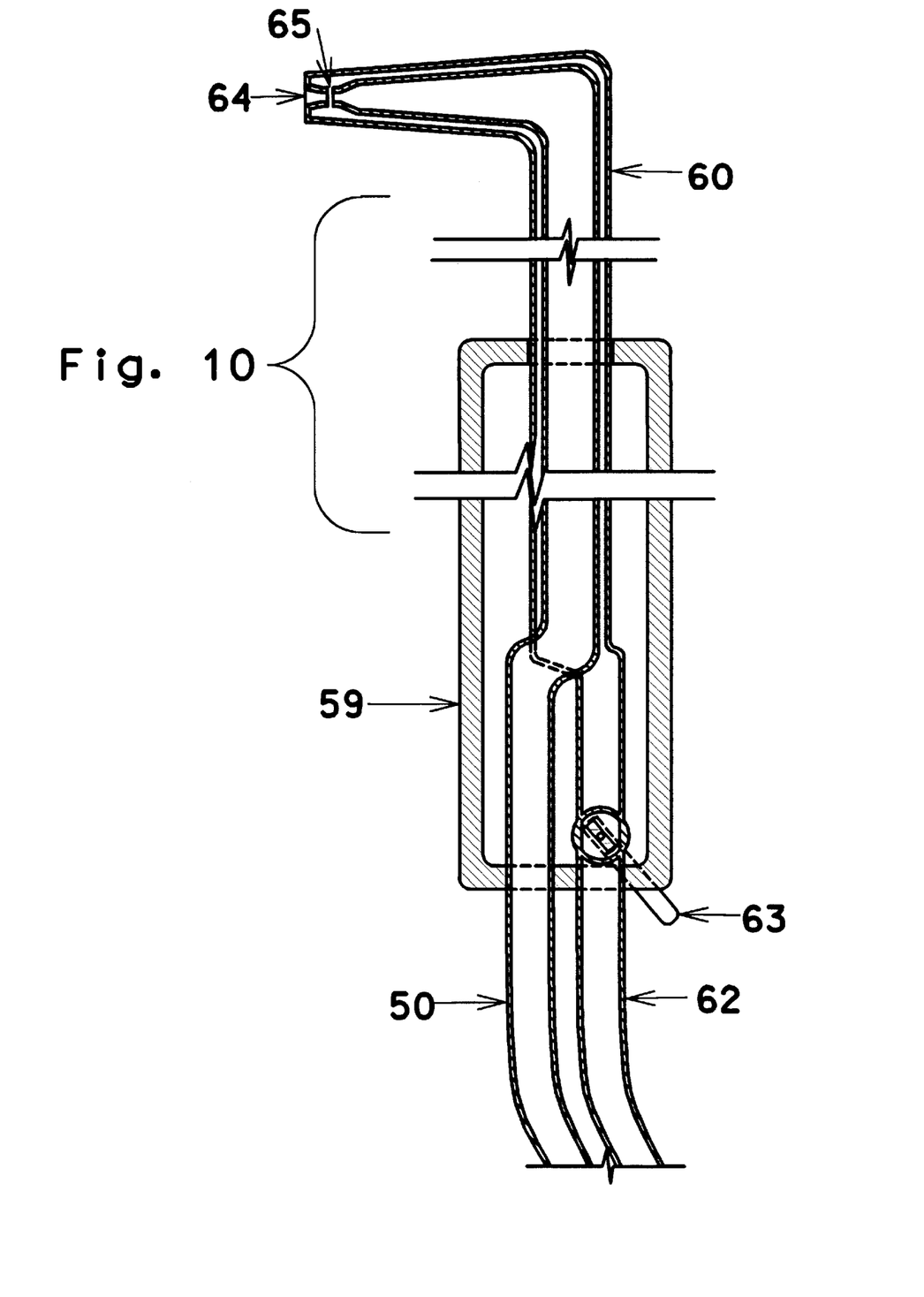
FIG. 10 is a sectional view of the components shown in FIG. 9.

Referring to FIGS. 9 and 10, one end of the handle 59 connects with the tubes 50 and 62. The other end of the handle connects with the discharging header 60. The discharging header consists of two concentric relatively rigid tubes with a sharp bend near its free end that the inner tube reduces its correctional area and becomes a nozzle 64. The outer tube opens (shown as 65) to the narrowest portion of the nozzle of the inner tube so that together they form a device similar to a jet pump. The handle facilities the handling and controlling of the discharging header. The handle also provides conduit to convey liquid from the tubes to the discharging header. For the tube 62, the handle has an optional flow control valve 63 which can regulate the amount of flow discharging through the outer tube to the inner tube at the nozzle. For the tube 50, the handle may have an optional flow control valve assembly (not shown) which can regulate the amount flow discharging through the inner tube to its nozzle.

Figure 11:
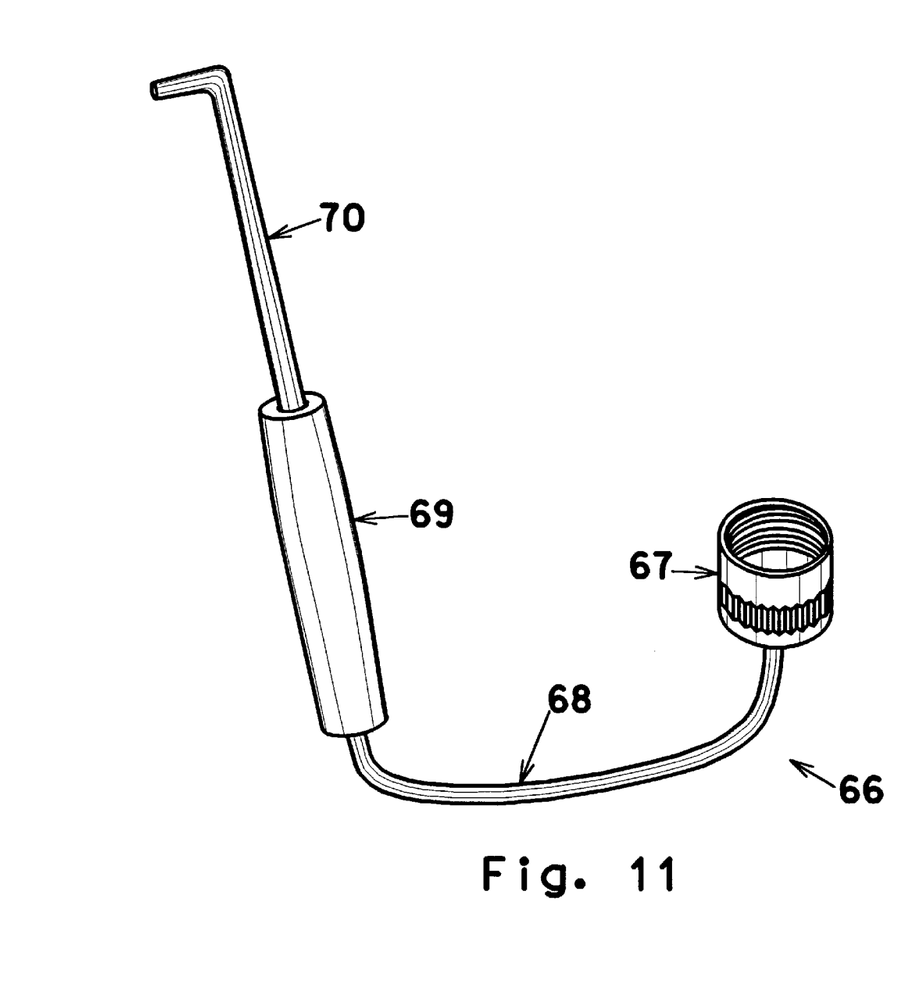
FIG. 11 is an isometric view of the fifth variation of the invented devices.

Referring to FIG. 11, the fifth variation of the invented portable water pick 66 consists of a bucket 67, a tube 68, a handle 69, and a discharging header 70. The tube, the handle and the discharge header are the same as those for the first variation of the invented devices. The bucket 67 is a small bucket that has a hole on its side wall or bottom. The tube 68 is mounted onto the bucket through the hole. There are screw threads at and near the rim of the bucket. The threads can be on the interior surface, on the exterior surface, or on both surfaces of the bucket. The threads can engage with those of spouts of ordinary faucets.

Although only the fourth variation of the invented devices is shown having a container, each of the other variations could have a container, a second tube and a handle and a discharging header the same as those of the fourth variation.

Figure 12:
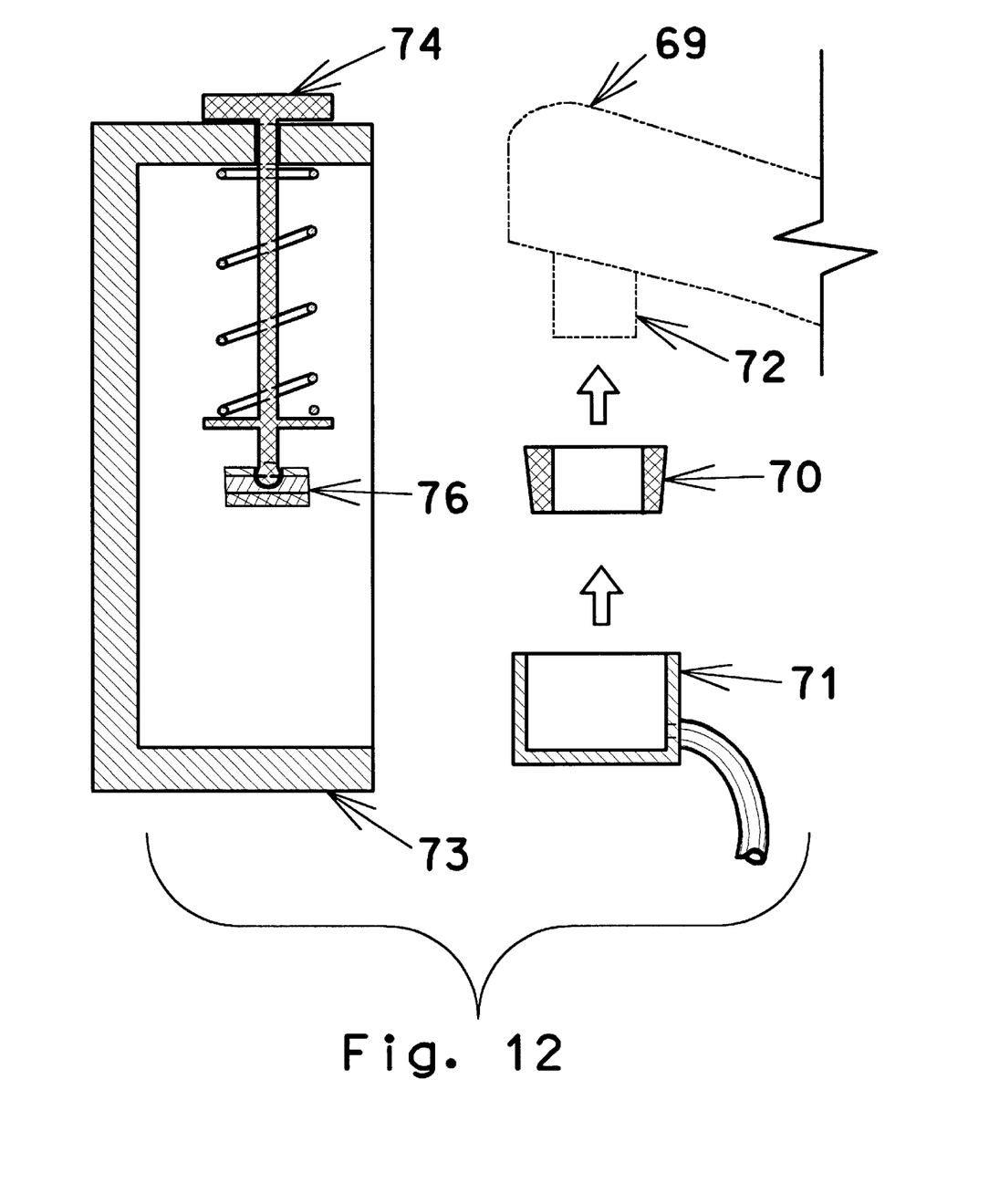
FIGS. 12, 13 and 14 are sectional views that illustrate the installation and removal of the components of the invented devices onto a sink faucet.
Figure 13:
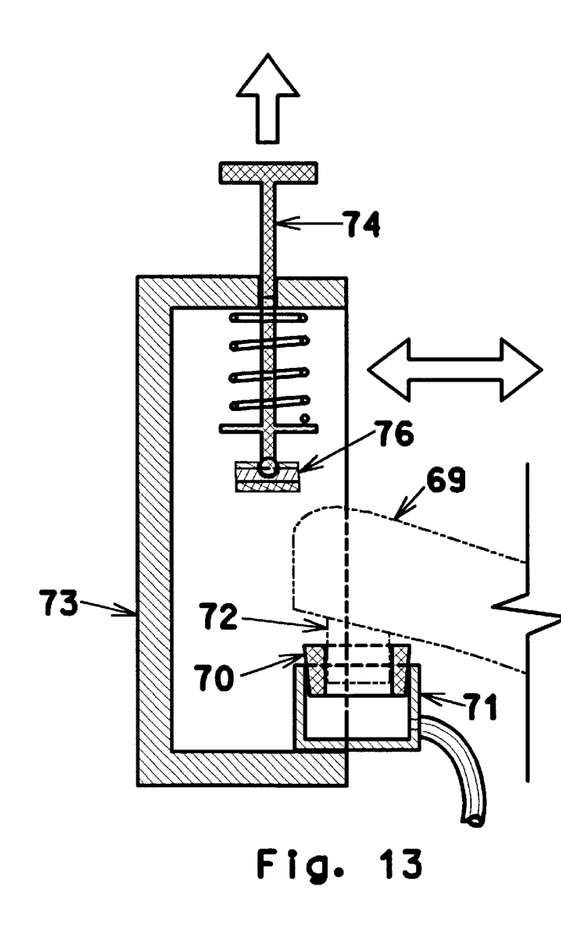
Figure 14:
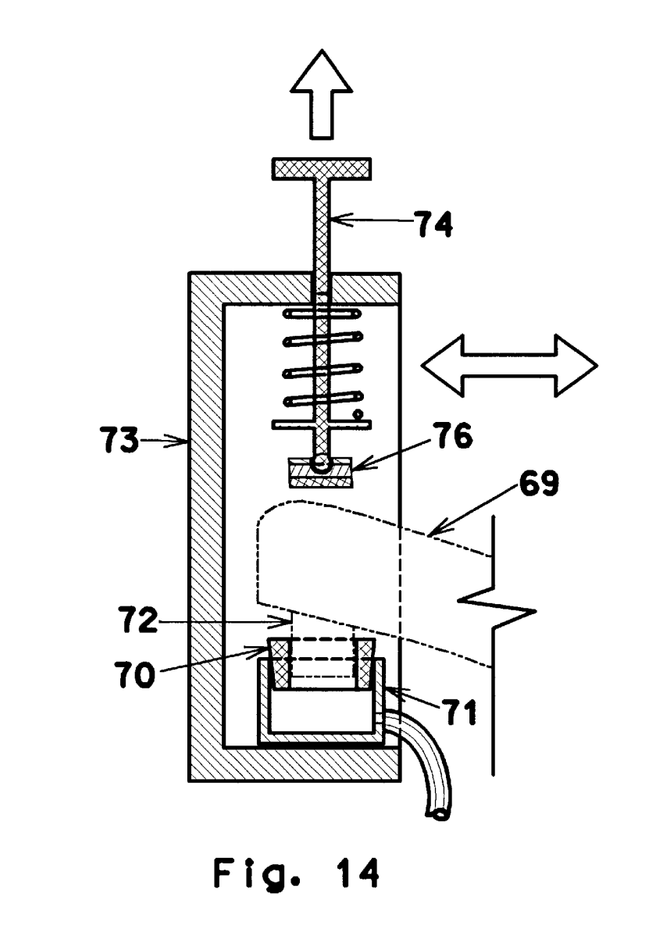

When using the invented devices, the bucket must be installed onto a faucet first. Referring to FIGS. 12, 13 and 14, in installing the first through the fourth variations of the invented devices, the cylindrical gasket 70 is firstly put on the exterior surface of an aerator 72 of a spout 69 of an existing faucet. The bucket 71 then is put onto the cylindrical gasket. The clamp 73 then is put onto the assembly by lifting up the spring-loaded adjuster 74 firstly, if the clamp of the third or the fourth variation of the invented devices is used, then sliding the clamp into position, as shown in FIGS. 13 and 14. The user then releases the spring-loaded adjuster so that its swivel head 76 pushes against the top of the sprout. The bucket then is pushed upwards by the bottom of the clamp. The rim of the clamp is pushed against the tapered exterior surface of the cylindrical gasket to create a watertight connection.

When the clamp of the first or the second variations of the invented devices is used, the user will release or tighten its adjusting bolts. Then the swivel head of the adjusting bolt will push against the top of the sprout that in turn pushes the bucket towards the cylindrical gasket to create a watertight connection.

The installation of a bucket of the fifth variation of the invented device just needs simply to screw the bucket onto the screw of the sprout of a faucet.

After the bucket of the first, the second, the third or the fifth variations of the invented devices being installed on a sprout, the user turns on the tap water so that a thin stream of water will shoot out from the nozzle of the discharging head of the devices. The user then uses the thin stream of water to pick up food residuals between teeth.

After the bucket of the fourth variations of the invented devices being installed on a sprout, the user put medicine or cleaning solutions in the container 61 and set the container on a surface 77, referring to FIG. 9. The user then turn on the tap water and a stream of water will shoot out from the nozzle of the discharging head of the invented devices. When the high speed tap water flows through the nozzle, it will suck the medicine or cleaning solutions out of the outer tube through its opening 65 to the nozzle, referring to FIG. 10. The optional flow control valves 63 can regulate the flow rate of the medicine or cleaning solutions being sucked out of the container. The user then uses the thin stream of water together with the medicine or cleaning solutions to pick up food debris and clean between teeth.

When a user finishes using the invented devices, the user may remove them from the faucet. The removal of the clamps, buckets, etc. from the sprout of an existing faucet will be reversals of the installations.

Figure 15:
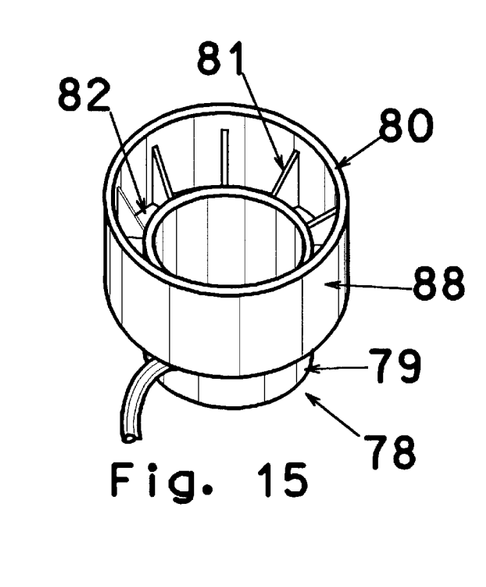
FIG. 15 is an isometric view of a modified bucket.

An accessory that can be added onto a bucket and a modification of the buckets are also introduced to deal with the occasionally spouted water from the joint between a bucket and a cylindrical gasket. Referring to FIG. 15, a modified bucket 78 consists of an added apron 88 attached to an aforementioned bucket 79 for the first through the fourth variations of the invented devices. The added apron consists of an outer spool 80 mounted by braces 81 onto the exterior surface of a bucket. The outer spool is a short spool. The top rim of the outer spool is higher than the rim of the bucket. The bottom rim of the outer spool is lower than the rim of the bucket. There are spaces 82 between the outer spool, the bucket, and two neighboring braces.

Figure 16:
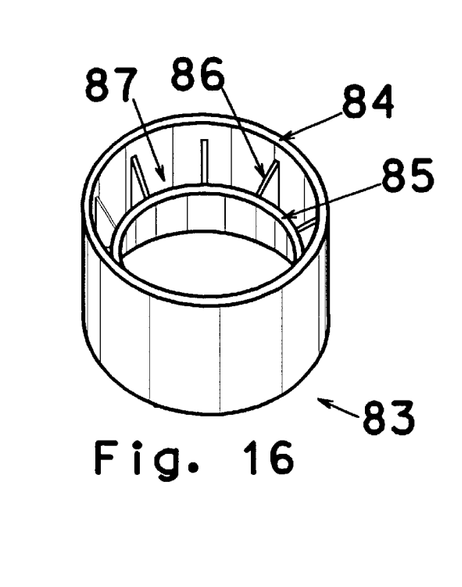
FIG. 16 is an isometric view of a removable apron for a bucket.

Referring to FIG. 16, a removable apron 83 consists of an inner spool 85 mounted by braces 86 onto an outer spool 84. The inner spool and the outer spool are spools. The top rim of the outer spool is higher than the top rim of the inner spool. The bottom rim of the outer spool is lower than the top rim of the inner spool. The inside diameter of the inner spool is slightly larger than the outside diameter of the aforementioned buckets for the first through the fourth variations of the invented devices. The removable apron therefore can be fitted onto a bucket. There are spaces 87 between the outer spool, the inner spool, and two neighboring braces.

The outer spool of the modified bucket will intercept any accidentally spouted water from the joint between a cylindrical gasket and a modified bucket. The spouted water then will drop through the gaps between the outer spool and the bucket into the sink below. When the removable apron is put on a bucket and is used, spouted water will drop below just like that in a modified bucket does.

Although cylindrical gaskets are illustrated, the gaskets may not have tapered surface. Instead, the buckets may have tapered interior surfaces. The action between the rim of the gasket and the tapered interior surface of the bucket will provide the joint. Furthermore, the gaskets or the buckets may not have tapered surface at all. The joint can exist between the tip of the gasket and the bottom of the bucket.

The foregoing is considered as illustrative only of the principles of the invention. Furthermore, since numerous modifications and changes will readily occur to those skilled in the art, it is not desired to limit the invention to the exact construction and operation shown and described, and accordingly all suitable modifications and equivalents, may be resorted to, falling within the scope of the invention as claimed.

I claim:
1. A portable water pick comprising in combination:
   a) a gasket for engaging an aerator of a spout of an existing sink;
   b) a bucket for engaging said gasket and for connecting with a flexible tube; said bucket having an apron which consists of a spool mounted by braces on the exterior surface of said bucket and which provides spaces for water to pass through;
   c) a clamp for squeezing said bucket and said gasket towards said spout of said existing sink;
   d) a handle which one end connects with said flexible tube and the other end connects with a discharging tube which has a bend near its free end;
   e) said handle being able to convey liquid from said flexible tube to said discharging tube.

2. A portable water pick comprising in combination:
   a) a gasket for engaging an aerator of a spout of an existing sink;
   b) a bucket for engaging said gasket and for connecting with a flexible tube; said bucket having an apron apparatus having inner and outer spools joined by braces; said inner spool removably engaging said bucket;
   c) a clamp for squeezing said bucket and said gasket towards said spout of said existing sink;
   d) a handle which one end connects with said flexible tube and the other end connects with a discharging tube which has a bend near its free end;
   e) said handle being able to convey liquid from said flexible tube to said discharging tube.

3. A portable water pick comprising in combination:
   a) a gasket for engaging an aerator of a spout of an existing sink;
   b) a bucket for engaging said gasket and for connecting with a flexible tube;
   c) a clamp for squeezing said bucket and said gasket towards said spout of said existing sink;
   d) said clamp having an adjustable screw which has a swivel head at one end and a handle on the other end;
   e) a handle which one end connects with said flexible tube and the other end connects with a discharging tube which has a bend near its free end;
   f) said handle being able to convey liquid from said flexible tube to said discharging tube.

4. A portable water pick comprising in combination:
   a) a gasket for engaging an aerator of a spout of an existing sink;
   b) a bucket for engaging said gasket and for connecting with a flexible tube;
   c) a clamp which can squeeze said bucket and said gasket towards said spout of said existing sink; said clamp having an adjuster which is a spring-loaded movable rod;
   d) a handle which one end connects with said flexible tube and the other end connects with a discharging tube which has a bend near its free end;
   e) said handle being able to convey liquid from said flexible tube to said discharging tube.

5. A portable water pick of claim 4 wherein said adjuster has a swivel head at one end and a handle on the other end.

6. A portable water pick comprising in combination:
   a) a gasket for engaging an aerator of a spout of an existing sink;
   b) a bucket for engaging said gasket and for connecting with a flexible tube;
   c) a clamp for squeezing said bucket and said gasket towards said spout of said existing sink;
   d) a container which connects with a flexible tube;
   e) a handle which one end connects with both said flexible tube connected to said bucket and said flexible tube connected to said container and which the other end connects with a discharging tube which has a bend near its free end;
   f) said discharging tube consisting of two tubes which outer tube connects with said flexible tube connected to said container and which inner tube connects with said flexible tube connected to said bucket;
   g) said inner tube of said discharging tube having a narrowing down section near its free end;
   h) said outer tube of said discharging tube connecting with said inner tube of said discharging tube at said narrowing down section;
   i) said handle being able to convey liquid from both said flexible tube connected to said bucket and said flexible tube connected to said container to said discharging tube.

7. A portable water pick of claim 6 wherein said gasket is a cylindrical gasket which has tapered exterior surface.

8. A portable water pick of claim 6 wherein said bucket has an apron which is a spool mounted by braces on the exterior surface of said bucket and which provides spaces for water to pass through.

9. A portable water pick of claim 6 wherein said bucket has an added on apron apparatus which consists of two spools joined by braces and which inner spool can engage with said bracket.

10. A portable water pick of claim 6 wherein said clamp has an adjustable screw.

11. A portable water pick of claim 10 wherein said adjustable screw has a swivel head at one end and a handle on the other end.

12. A portable water pick of claim 6 wherein said clamp has an adjuster which is a spring-loaded movable rod.

13. A portable water pick of claim 12 wherein said adjuster has a swivel head at one end and a handle on the other end.

14. A portable water pick of claim 6 wherein said handle has a valve assemble which can regulate flow rates through said handle.

15. A portable water pick of claim 6 wherein said handle has two valve assembles which can regulate flow rates through said handle.

16. A portable water pick comprising in combination:
   a) a bucket which rim has screw threads and which connects with a flexible tube;
   b) said screw threads of said bucket being able to engage with screw threads of a spout of an existing sink;
   c) a container which connects with a flexible tube;
   d) a handle which one end connects with both said flexible tube connected to said bucket and said flexible tube connected to said container and which the other end connects with a discharging tube which has a bend near its free end;

e) said discharging tube consisting of two tubes which outer tube connects with said flexible tube connected to said container and which inner tube connects with said flexible tube connected to said bucket;

f) said inner tube of said discharging tube having a narrowing down section near its free end;

g) said outer tube of said discharging tube connecting with said inner tube of said discharging tube at said narrowing down section;

h) said handle being able to convey liquid from both said flexible tube connected to said bucket and said flexible tube connected to said container to said discharging tube.

17. A portable water pick of claim 16 wherein said handle has a valve assemble which can regulate flow rates through said handle.

18. A portable water pick of claim 16 wherein said handle has two valve assembles which can regulate flow rates through said handle.

* * * * *